United States Patent [19]

Birum

[11] 4,003,965
[45] Jan. 18, 1977

[54] PHOSPHORUS COMPOUNDS
[75] Inventor: Gail H. Birum, Kirkwood, Mo.
[73] Assignee: Monsanto Company, St. Louis, Mo.
[22] Filed: June 23, 1975
[21] Appl. No.: 589,097

Related U.S. Application Data
[63] Continuation-in-part of Ser. No. 385,931, Aug. 6, 1973, Pat. No. 3,920,733.
[52] U.S. Cl. .............................. 260/932; 260/968; 260/969
[51] Int. Cl.² ........................................ C07F 9/40
[58] Field of Search .................. 260/932, 968, 969
[56] References Cited
UNITED STATES PATENTS

| 2,635,112 | 4/1953 | Fields | 260/932 X |
| 3,763,108 | 10/1973 | Chang et al. | 260/969 X |
| 3,763,281 | 10/1973 | Weil | 260/932 |

Primary Examiner—Richard L. Raymond

[57] ABSTRACT

The present invention relates to new nitrogen-containing organophosphorus compounds having chloro- or bromoalkyloxy substituents bonded to phosphorus in ester structures.

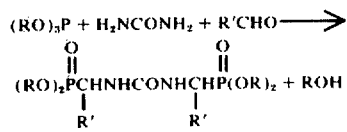

R is haloalkyl of 2 to 5 carbon atoms, and
R' is alkyl or alkenyl of 1 to 15 carbon atoms.

The phosphorus compounds have utility as fire retardants and as biologically active materials.

2 Claims, No Drawings

PHOSPHORUS COMPOUNDS

The present patent application is a continuation-in-part of Ser. No. 385,931, filed Aug. 6, 1973, now U.S. Pat. No. 3,920,733.

The present invention relates to new nitrogen-containing organophosphorus compounds having chloro- or bromoalkyloxy substituents bonded to phosphorus in ester structures. The products can be hydrolyzed to the corresponding acids.

A new process for the production of such compounds is also a part of the present invention.

The general method for the production of the novel nitrogen-containing organophosphorus compositions is in accordance with the equation shown below:

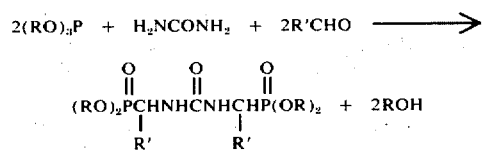

where
R is chloro- or bromoalkyl of 2 to 5 carbon atoms, and
R' is alkyl or alkenyl of 1 to 15 carbon atoms.
A specific compound is:

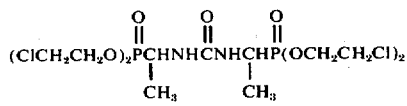

If at least two molar proportions of both $(RO)_3P$ and R'CHO are used relative to $H_2NCONH_2$, and the temperatures and time employed are sufficient to complete the reaction, the diphosphorus-containing product may be obtained essentially exclusively. However, if the reactants $(RO)_3P$ and R'CHO are used in less than two molar proportions relative to the third reactant, $H_2NCONH_2$, a monophosphorus product is usually obtained along with the diphosphorus product of this invention.

Formation of the compounds of this invention is usually initiated when a mixture of the three reactants is warmed to about 70° C. The reaction is usually complete after 1 hour at 80°–120° C., but warming at lower or higher temperatures is sometimes advantageous. An alternate procedure, which may facilitate control of heat of reaction, is to gradually add the aldehyde reactant to a stirred mixture of the phosphorus ester and urea reactants at reaction temperature, generally from about 70° to 120° C. The use of an inert solvent, for example, toluene, chlorobenzene, and 1,2-dichloroethane, may sometimes be beneficial.

In cases where a mixture of mono- and diphosphorus-containing ester products are produced by using less than two molar proportions of $(RO)_3P$ and R'CHO relative to $H_2NCONH_2$, it has generally been found that selective hydrolysis of the monophosphorus ester can be accomplished by treating the crude mixture of esters with at least a stoichiometric quantity of water at a temperature in the range of 10° to 150° C. The relatively insoluble monophosphorus acid thus produced can be readily separated from the unhydrolyzed diphosphorus ester by standard techniques such as filtration. The diphosphorus esters can normally be hydrolyzed to the corresponding acids at higher temperatures than needed for the monophosphorus esters, or the hydrolysis can usually be accomplished more readily by the use of dilute aqueous acids such as hydrochloric acid, hydrobromic acid, and sulfuric acid.

Specific examples showing the preparation and isolation of representative compounds of the present invention are set forth herewith, but are not limitative of the scope of the invention.

EXAMPLE 1

Tetrakis(2-chloroethyl) (ureylenediethyl)diphosphonate

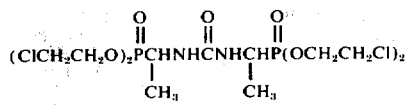

A 2-liter, 4-necked flask equipped with a thermometer, mechanical stirrer, dropping funnel, and dry ice-cooled condenser is swept with nitrogen and charged with 539.0g (2.0 moles) of crude tris(2-chloroethyl) phosphite, 60.0g (1.0 mole) of powdered urea, and one-half of 94.6g (2.15 moles) of freshly distilled acetaldehyde. When this mixture is warmed, refluxing begins at 47° C and the temperature is gradually increased to 60° in 25 minutes. The mantle is removed, and the heat of reaction raises the temperature to 82° in 15 minutes. The remainder of the acetaldehyde is then added below the surface of the reaction mixture in 11 minutes at 65°–75°. Warming at 90°–95° for 0.5 hr gives a clear, colorless solution: $^{31}P$ nmr $-27.6$ ppm. One pint of 1,2-dichloroethane is added, and the solution is washed five times with 400 ml portions of water and then stripped to 110° /0.2mm to give 469g (89%) of colorless, viscous liquid: $n_D^{25}$ 1.4991; $^{31}P$ nmr $-27.8$ ppm; molecular weight (acetone) 520 (calcd 526).

Anal. Calcd for $C_{13}H_{26}Cl_4N_2O_7P_2$: C, 29.67; H, 4.98; Cl, 26.95; N, 5.32; P. 11.77. Found: C, 29.75; H, 5.08; Cl, 27.00; N, 5.22; P, 11.63. A solid forms after a portion of the viscous liquid is several times diluted with acetone and finally with ether and the solvent allowed to evaporate each time. Recrystallization twice from acetonitrile-ether gives a white solid: mp 138°–140°; $^{31}P$ nmr $-27.8$ ppm(m); $^1H$ nmr δ6.45 (d, 2, J = 10Hz, NH), 4.1 to 4.8 (m, 10, $POCH_2$ and PCH), 3.5 to 3.9 (m, 8, $ClCH_2$), 1.38 (d of d, 6, J = 17 and 7Hz, $CH_3$); ir (KBr) 2.97 (m), 3.33(w), 5.89(s), 6.38(s), 6.83(m), 7.93(s), 8.13(s), 9.2(s), 6.65μ (vs); molecular weight (DMF) 516.

Anal. Found: C, 29.97; H, 5.09; Cl, 26.99; N, 5.28; P, 11.71.

When 1 mole of urea is similarly treated with at least 2 moles each of tris(2-chloroethyl)phosphite and 2-ethylexaldehyde, the product is tetrakis(2-chloroethyl) [urylenedi(2-ethylhexyl]diphosphonate, $^{31}P$ nmr $-27$ppm.

Similarly, the treatment of urea with at least 2 moles each of tris(2-chloropropyl)phosphite and 10-undecenal gives the product tetrakis(2-chloropropyl) [urylenedi(10-undecenyl)]di-phosphonate, $^{31}P$ nmr $-27$ppm.

EXAMPLE 2

Tetrakis(1-bromo-3-chloro-iso-propyl) (ureylenediethyl)diphosphonate

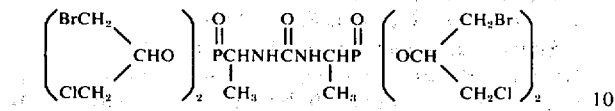

When a mixture of 548.3g (1.0 mole) of crude tris (1-bromo-3-chloro-iso-propyl) phosphite, 30.0g (0.5 mole) of powdered urea, and 48.4g (1.1 moles) of redistilled acetaldehyde in 300g of 1,2-dichloroethane is stirred under nitrogen without warming, the temperature increases spontaneously from 24° to 78° C in 43 minutes before subsiding. The reaction mixture is then warmed at 85°–90° for 0.5 hr, giving a brown solution; $^{31}$P nmr −27.0 ppm(m). Stripping to 117°/10.5mm gives 482g of viscous, red-brown liquid. A 50g portion is twice stirred in ether and the ether allowed to evaporate to give a mixture of solid and red oil. The solid is separated by suction filtration and then recrystallized from acetone to give 16.6g mp 140°–148°. Recrystallization of a portion from acetone gives white solid: mp 145°–148°; $^{31}$P nmr −27.1 ppm(m); $^1$H nmr δ6.30 (d, 2, J = 8.5Hz, NH). 4.75 (m, 6, CHO and CHN), 3.78 (m, 16, CH$_2$Br and CH$_2$Cl), 1.42 (d of d, 6, J = 18 and 7Hz, CH$_3$); molecular weight (acetone) 898 (calcd 898).

Anal. Calcd for C$_{17}$H$_{30}$Br$_4$Cl$_4$N$_2$O$_7$P$_2$: Br, 35.58; Cl, 15.79; N, 3.12; P, 6.90. Found: Br, 35.47; Cl, 15.62; N, 2.86; P, 6.74.

EXAMPLE 3

Bis(2-chloroethyl) 1-sulfamidobutylphosphonate

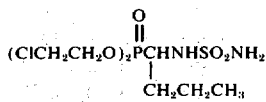

When a mixture of 0.55 mole of tris(2-chloroethyl) phosphite, 0.50 mole of n-butyraldehyde, and 0.50 mole of sulfamide is warmed to 85° C, a reaction is initiated, and cooling is needed for a few minutes to keep the temperature below 100°. The reaction mixture is warmed at 95°–100° for 0.5 hr. and then stripped to 100° at 0.5 mm. The addition of 150 ml. of ether to the residue and cooling causes a solid to separate. This is separated, washed with water, and recrystallized from benzene to give a white solid: mp 85°–87°; $^{31}$P nmr −25.6 ppm.

Anal. Calcd for C$_8$H$_{19}$Cl$_2$N$_2$O$_5$PS: C, 26.90; H, 5.36; Cl, 19.85; N, 7.84; P, 8.67; S, 8.98. Found: C, 27.14; H, 5.46; Cl, 20.25; N, 7.99; P, 8.58; S, 9.05.

Similar treatment of equimolar quantities of tris(2-chloroethyl) phosphite, sulfamide, and p-bromophenylacetaldehyde or, in another synthesis, p-trifluoromethyl phenylacetaldehyde, gives bis(2-chloroethyl) 1-sulfamido-2-p-bromophenylethylphosphonate and bis(2-chloroethyl) 1-sulfamido-2-p-trifluoromethylphenyl-ethylphosphonate, respectively. Hydrolysis of these phosphonate esters gives the corresponding phosphonic acids.

EXAMPLE 4

1-Ureidopropylphosphonic acid

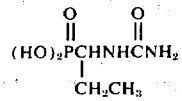

Freshly distilled propionaldehyde, 58.0g (1.0 mole), is added dropwise in 1 hr to a stirred mixture of 60.0g (1.0 mole) of powdered urea and 269.5g (1.0 mole) of crude tris (2-chloroethyl) phosphite at 105°–112° C. Heat of reaction keeps the temperature at this level without external warming during most of the aldehyde addition. The reaction mixture is warmed for 0.25 hr more, and then it is stripped to 122°/2mm, giving a viscous, yellow residue, crude bis(2-chloroethyl) 1-ureidopropylphosphonate. This is dissolved in 100ml of acetonitrile and 36g (2.0 moles) of water, and the solution is warmed at reflux for 1 hr. A solid forms during warming and is separated by filtration of the warm reaction mixture; and then it is stirred and warmed in more acetonitrile and water, and the mixture is filtered while warm to give 76.2g (42%) of white solid, mp 185°–186° dec. A 5.0-g portion is recrystallized from acetic acid-water to give 3.2g: mp 189°–191° dec; $^{31}$P nmr (CD$_3$SOCD$_3$) −23.0 ppm(m); $^1$H nmr δ 8.5 (broad, 4, O$\underline{H}$ and N$\underline{H}_2$), 6.2 (broad, 1, NH), 3.7 (broad, 1, CH), 1.6 and 0.9 (broad, 5, C$\underline{H}_2$C$\underline{H}_3$); acidity 2.01 equiv/mole, pK$_1$ 2.70, pK$_2$ 7.30.

Anal. Calcd for C$_4$H$_{11}$N$_2$P: C, 26.38; H, 6.09; N, 15.38; P, 17.01. Found: C, 26.50; H, 6.11; N, 15.26; P, 16.99.

EXAMPLE 5

Tetrakis(2-chloroethyl)[urylenedi(2-methylpropyl)] diphosphonate and [Urylenedi(2-methylpropyl)] diphosphonic acid.

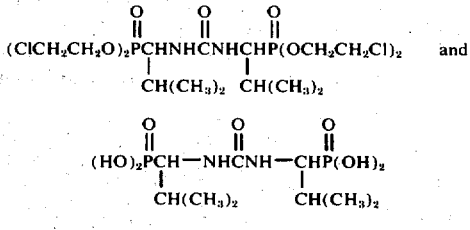

Tetrakis(2-chloroethyl) [urylenedi(2-methylpropyl)] diphosphonate (A) is prepared from tris(2-chloroethyl)phosphite, urea, and iso-butyraldehyde by a procedure similar to that used for the preparation of Example 1. When a solution of 11.8g (0.02 mole) of A, mp 146°–150°, and 2.9g (0.16 mole) of distilled H$_2$O in 75ml of acetonitrile is warmed at reflux for 7 hr, A is recovered unchanged. The recovered A is then stirred at reflux with 2.9g of distilled H$_2$O and 1 ml of concentrated hydrochloric acid in 75ml of acetonitrile for 6 hr. A solid, 4.4g (67%), that separates during this warming period is recrystallized from CH$_3$CN—H$_2$O and then from CH$_3$CO$_2$H—H$_2$O to give the white solid product: mp (appears to melt at 215°, resolidifies and then remelts at 275°–280° with foaming); $^{31}$P nmr (DMSO-d$_6$) −22.8 ppm(m); $^1$H nmr δ8.6(s, 5, $\underline{H}$O and N$\underline{H}$), 6.3 (broad, 1, NH), 3.8 (m, 2, CHP), 2.0 [m, 2, C$\underline{\text{H}}$(CH$_3$)$_2$]; acidity by potentiometric titration 4.10 equiv/mole, pK$_1$ = 2.71, pK$_2$ = 8.24.

Anal. Calcd for C$_9$H$_{22}$N$_2$O$_7$P$_2$: C, 32.54; H, 6.68; N, 8.43 P, 18.64. Found: C, 32.64; H, 6.40; N, 8.35; P, 18.51.

EXAMPLE 6

Tetramethyl [urylenedi(2-methylpropyl)]diphosphonate

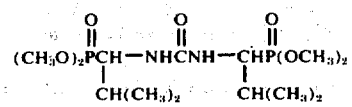

A mixture of 2.0g of (5) in 24g of trimethyl orthoformate is warmed at reflux for 18 hr. Low boilers are removed by fractionation through a short column during the reflux period. The excess orthoformate is then distilled at reduced pressure, and the residue is diluted with ether, and this mixture is filtered to give 0.5g of solid. Recrystallization from acetone gives tetramethyl-[urylenedi(2-methylpropyl)]diphosphonate, a white solid: mp 182°–184.5°; $^{31}$P nmr (CDCl$_3$) −27.7 ppm; $^1$H nmr δ6.61 (d, 2, J = 10Hz, CHN$\underline{\text{H}}$), 4.3 (four doublets, 2, J$_{CH\text{-}P}$ = 18Hz, J$_{CH\text{-}NH}$ = 10Hz, J$_{CH\text{-}CH}$ = 4Hz, PC$\underline{\text{H}}$(CH)NH), 3.76 (d, 6, H$_{CH3OP}$ = 10Hz), 3.73 (d, 6, J$_{CH3OP}$ = 10Hz), 2.06 [m, 2, C$\underline{\text{H}}$(CH$_3$)$_2$], 1.03 [D, 12, J = 7Hz, CH(C$\underline{\text{H}}$$_3$)$_2$]; ir (KBr) 2.84(w), 3.00(m), 3.37(m), 5.93(s), 6.73(s), 6.79(m), 7.72(m), 8.04(vs).

EXAMPLE 7

Diethyl α-(3-phenylureido)benzylphosphonate

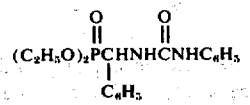

A $^{31}$P nmr measurement indicates that there is only a slow reaction when a mixture of 0.30 mole of triethyl phosphite, 0.30 mole of phenylurea, and 0.33 mole of benzaldehyde in 150g of toluene is warmed at 95°–100° for 0.5 hr. Boron trifluoride etherate (0.05 mole) is then added dropwise, causing a temperature rise. The reaction mixture is warmed at 95°–100° for 1 hr and then stripped to a pot temperature of 120°/10mm. The residue is diluted with ether, causing separation of a solid (75.7g, including additional fractions from the filtrate). Recrystallization of a portion from acetonitrile gives a white solid: mp 150°–151.5°; $^{31}$P nmr (CDCl$_3$) −23.1 ppm; $^1$H nmr δ8.35 (s, 1, NHC$_6$H$_5$), 6.7–7.8 (m, 11, C$_6$H$_5$ and CHN$\underline{\text{H}}$), 5.6 (d of d, 1, J$_{H\text{-}P}$ = 22Hz, J$_{HH}$ = 10Hz, C$\underline{\text{H}}$NH), 3.5–4.6 (m, 4, C$\underline{\text{H}}$$_2$CH$_3$), 1.25 (overlapping triplets, 6, CH$_2$C$\underline{\text{H}}$$_3$).

Anal. Calcd for C$_{18}$H$_{23}$N$_2$O$_4$P: C, 59.66; H, 6.40; N, 7.73; P; 8.55. Found: C, 59.60; H, 6.41; N, 7.65; P, 8.69.

When the above preparation is modified by using citral instead of benzaldehyde, the product is diethyl 1-(3-phenylureido)-3,7-dimethylocta-2,6-dienyl-1-phosphonate.

EXAMPLE 8

This example shows the preparation of a phosphinate compound, i.e., a compound having two P—C bonds. It also shows the use of a thiourea as a reactant. When equimolar quantities of bis(2-chloroethyl) methylphosphonite, p-chlorophenylacetaldehyde, and phenylthiourea are warmed at 90°–110° C for 1 hour, 2-chloroethyl [1-(3-phenylthioureido)-2-(p-chlorophenyl) ethyl]methylphosphinate is formed. Hydrolysis gives the corresponding phosphinic acid.

This example shows the preparation of a phosphine oxide, that is a compound containing three P—C bonds. Warming (50°–100° C) of a mixture of ethyl dimethylphosphinite, acetaldehyde and urea in the presence of a catalytic amount of boron trifluoride etherate gives dimethyl (1-ureidoethyl)phosphine oxide, a product that cannot be hydrolyzed to an acid of phosphorus.

When the above preparation is modified by using methyl-urea instead of urea, the product is dimethyl [1-(3-methylureido)ethyl]phosphine oxide.

EXAMPLE 9

2-Ethyl-1-ureidohexylphosphonic acid

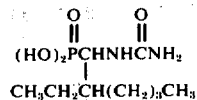

This compound is prepared from urea, tris(2-chloroethyl) phosphite, 2-ethylhexaldehyde, and water under conditions similar to those used for the preparation of 1-ureidopropyl-phosphonic acid in Example 4. The product is obtained as a white solid: mp 206° C dec; $^{31}$P nmr (CD$_3$SOCD$_3$) −23.2 ppm; $^1$H nmr δ8.5 (broad, 4, $\underline{\text{H}}$O and N$\underline{\text{H}}$$_2$), 6.2 (d, 1, J = 8Hz, NH), 4.3 (d, of d, 1, J = 8 and 20Hz, PCH), 1.3 and 0.9 (m, 15); acidity 2.00 equiv/mole, pK$_1$ = 3.50, pK$_2$ = 9.08.

Anal. Calcd for C$_9$H$_{21}$O$_4$N$_2$P: C, 42.85; H, 8.39; N, 11.11; P, 12.21. Found: C, 42.89; H, 8.29; N, 11.09; P, 12.23.

EXAMPLE 10

1(3,3-Diphenylureido)ethylphosphonic acid

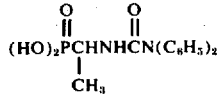

Freshly distilled acetaldehyde (0.22 mole) is added during 0.5 hr to a stirred solution of 0.1 mole each of 1,1-diphenylurea and triphenyl phosphite in 130g of benzene at 60° C. The solution is warmed at reflux (65°–70° with a Dry Ice-cooled condenser) for 1.25 hr, giving a dark brown solution having a small $^{31}$P nmr peak at −126.2 ppm for unrected phosphite and a large product peak at −18.4 ppm (∼1:5 areas). The reaction mixture is stripped to 130°/3mm and the residue diluted with 200 ml of acetonitrile and 10g of H$_2$O, and this solution warmed at reflux for 3 hr. Solid that separates during warming is recrystallized from acetic acid-water to give the product as a white solid: mp 186°–187° C dec; P$^{31}$ nmr −21.6 ppm; $^1$H nmr δ10.0 (s, 2, OH), 7.3 (m, 10, C$_6$H$_5$), 5.4 (d of d, 1, J = 9 and 5Hz, NH), 4.1 (m, 1, CH), 1.3 (d, of d, 3, J = 16 and 7 Hz, CH$_3$); acidity 2.00 equiv/mole, pK$_1$ = 2.20, pK$_2$ = 8.62.

Anal. Calcd for C$_{15}$H$_{17}$N$_2$O$_4$P: C, 56.25; H, 5.35; N, 8.75; P, 9.67. Found: C, 56.43; H, 5.36; N, 8.84; P, 9.60.

EXAMPLE 11

Pre-emergent herbicidal activity of representative compounds of this invention is determined by the following procedure:

A good grade of top soil is placed in aluminum pans and compacted to a depth of ⅜ to ½ inch from the top of the pan. A pre-determined number of seeds of each of several plant species are placed on top of the soil in the pans. The seeds are covered with soil and the pans leveled. The herbicidal composition is applied by spraying the surface of the top layer of soil with a solution containing a sufficient amount of active ingredient to obtain a rate of application of 10 lbs. per acre. The pans are then placed on a sand bench in the greenhouse and watered from below as needed. The plants are observed at the end of approximately 14 days and the results recorded.

Pre-emergent activity of the compounds prepared in the designated examples is observed against the species as shown in the table below, wherein X denotes the herbicidal activity observed. In general compounds having the formula

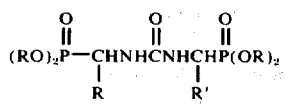

where R is chloro or bromoalkyl of 1 to 5 carbon atoms, and R' is alkyl or alkenyl of 1 to 15 carbon atoms are useful in this relationship, such as tetrakis(2-chloroethyl)(urylenediethyl)diphosphonate, and tetrakis(2-chloroethyl)[urylenedi(2-methylpropyl)]diphosphonate, and tetrakis(2-chloroethyl[urylenedi(2-ethylhexyl)]diphosphonate, and tetrakis(2-chlorophenyl)[urylenedi(10-undecenyl)]diphosphonate, and tetrakis(1-bromo-3-chloro-iso-propyl) (urylenediethyl)diphosphonate.

| PRE-EMERGENT TESTING | | |
|---|---|---|
| Compound of Example | 1 | 2 |
| General Narrowleaf | X | X |
| General Broadleaf |  | X |
| Canada Thistle | X | X |
| Cocklebur | X |  |
| Velvetleaf | X |  |
| Morning Glory | X | X |
| Lambsquarters | X |  |
| Smartweed | X | X |
| Nutsedge | X | X |
| Quackgrass |  | X |
| Johnsongrass | X | X |

The nitrogen-containing organophosphorus compounds of the present invention are useful as fire-retardants and as biological toxicants. The following examples illustrate the use of typical products.

A preliminary fire-retardant test is conducted as follows:

A 2 inches × 8 inches strip of cotton cloth is padded with a solution of equal parts of the test compound and 37% formalin, and the strip is dried at 65° C and then cured at 140° C for 0.5 hr. This is followed by washing with water and then with acetone and drying to constant weight. This treated sample is applied to a Bunsen burner and then removed from the combustion zone of the burner after 5 seconds exposure to the flame. A sample which is self-extinguishing after this treatment is considered to pass the test. When tetrakis(2-chloroethyl) (ureylenediethyl)diphosphonate) is used, and the add-on is about 15%, the sample passes the test. Another representative compound of the invention which has fire-retardant properties is tetrakis(1-bromo-3-chloro-iso-propyl) (urylenediethyl)diphosphonate.

Another fire retardant test employed in the present research is ASTM method D1230-52T applied to nonwoven fabrics of about 70 wt % cotton and 30 wt % nylon. This test uses a 2 inches × 5 inches sample impregnated with the neat phosphorus compound (no formaldehyde adduct) at various loadings, as shown below. The time required for the sample to be consumed is reported as the average of 5 tests:

| Loading Wt.% | Time Required | |
|---|---|---|
| 0% | 4.2 | sec. |
| 5% | 10.1 | sec. |
| 7.5% | 14.0 | sec. |
| 10% | 17.6 | sec. for 2 samples (3 samples would not ignite) |

The above test is used with tetrakis(2-chloroethyl) (urylen-ediethyl) as the test chemical.

Compounds of this invention that contain at lease ten percent halogen (especially chlorine and bromine) are particularly useful as fire-retardants.

In general compounds having the formula

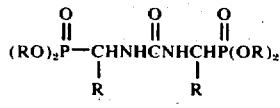

where R chloro or bromoalkyl of 1 to 5 carbon atoms, and R' is alkyl or alkenyl of 1 to 15 carbon atoms are useful in this relationship, such as tetrakis(2-chloroethyl)(urylenediethyl)diphosphonate, and tetrakis(2-chloroethyl)[urylenedi(2-methylpropyl)]diphosphonate, and tetrakis(2-chloroethyl)[urylenedi(2-ethylhexyl)diphosphonate, and tetrakis(2-chloropropyl)-[urylenedi(10-undecenyl)]diphosphonate, and tetrakis(1-bromo-3-chloro-iso-propyl) (urylenediethyl)diphosphonate.

What is claimed is:

1. A compound of the formula

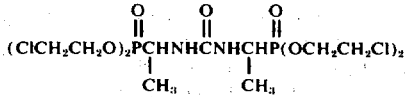

2. One-step process for the production of a compound of the formula

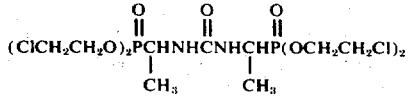

which comprises heating $H_2NCONH_2$ with two molar proportions of $(ClCH_2CH_2O)_3P$ and $CH_3CHO$ relative to $H_2NCONH_2$.

* * * * *